United States Patent [19]

Varona

[11] Patent Number: 6,150,002

[45] Date of Patent: Nov. 21, 2000

[54] CREPED NONWOVEN LINER WITH GRADIENT CAPILLARY STRUCTURE

[75] Inventor: Eugenio Go Varona, Marietta, Ga.

[73] Assignee: Kimberly-Clark Worldwide, Inc., Neenah, Wis.

[21] Appl. No.: 09/040,707

[22] Filed: Mar. 18, 1998

Related U.S. Application Data

[63] Continuation-in-part of application No. 08/962,992, Oct. 31, 1997.

[51] Int. Cl.$^7$ .............................. B32B 3/06; B32B 5/02; D06N 7/04

[52] U.S. Cl. .......................... 428/99; 428/152; 428/195; 428/198; 422/149; 422/401

[58] Field of Search .................................. 442/328, 401, 442/149, 150; 428/99, 152, 195, 198

[56] References Cited

U.S. PATENT DOCUMENTS

| | | |
|---|---|---|
| 3,668,054 | 6/1972 | Stumpf . |
| 3,687,754 | 8/1972 | Stumpf ..................................... 156/72 |
| 3,694,867 | 10/1972 | Stumpf . |
| 3,705,065 | 12/1972 | Srumpf . |
| 3,720,554 | 3/1973 | Stumpf . |
| 3,802,817 | 4/1974 | Matsuki et al. . |
| 3,849,241 | 11/1974 | Butin et al. . |
| 3,879,257 | 4/1975 | Gentile et al. . |
| 3,881,490 | 5/1975 | Whitehead et al. ..................... 128/287 |
| 3,949,128 | 4/1976 | Ostermeier .............................. 428/152 |
| 4,000,237 | 12/1976 | Roberts, Jr. ............................. 264/128 |
| 4,125,659 | 11/1978 | Klowak et al. .......................... 428/153 |
| 4,127,637 | 11/1978 | Pietreniak et al. ...................... 264/114 |
| 4,158,594 | 6/1979 | Becker et al. ........................... 162/112 |
| 4,326,000 | 4/1982 | Roberts, Jr. ............................. 428/153 |
| 4,422,892 | 12/1983 | Plant ....................................... 156/209 |
| 4,810,556 | 3/1989 | Kobayashi et al. . |
| 4,892,557 | 1/1990 | Conklin et al. . |
| 5,102,724 | 4/1992 | Okawahara et al. . |
| 5,108,820 | 4/1992 | Kaneko et al. . |
| 5,108,827 | 4/1992 | Gessner . |
| 5,270,107 | 12/1993 | Gessner . |
| 5,336,552 | 8/1994 | Strack et al. . |
| 5,382,400 | 1/1995 | Pike et al. . |
| 5,468,796 | 11/1995 | Chen et al. .............................. 524/377 |
| 5,543,202 | 8/1996 | Clark et al. . |
| 5,614,281 | 3/1997 | Jackson et al. ......................... 428/100 |
| 5,623,888 | 4/1997 | Zafiroglu . |
| 5,669,900 | 9/1997 | Bullwinkel et al. .................... 604/391 |
| 5,728,081 | 3/1998 | Baer et al. .............................. 604/370 |
| 5,846,232 | 12/1998 | Serbiak et al. ....................... 604/385.2 |

FOREIGN PATENT DOCUMENTS

| | | | |
|---|---|---|---|
| 064 853 | 11/1982 | European Pat. Off. ......... | D04H 1/54 |
| 0586924 | 3/1994 | European Pat. Off. . | |
| 97 19808 | 6/1997 | WIPO .............................. | B32B 5/02 |

OTHER PUBLICATIONS

John A. Manson and Leslie H. Sperling: *Polymer Blends and Composites*, 1976, Plenum Press, a division of Plenum Publishing Corporation of New York, IBSN 0–306–30831–2, pp. 273–277.

A.A. Burgeni and Kapur: Capillary Sorption Equilibria in Fiber Masses, Textile Research Journal, vol. 37, pp. 356–366 (1967).

Frank J. Akin, Jac T. Lemmen, Dena L. Bozarth, Martin J. Garofalo and Gary L. Grove: A refined method to evaluate diapers for effectiveness in reducing skin hydration using the adult forearm, Skin Research and Technology, 1997, vol. 3, pp. 173–176.

*Primary Examiner*—Blaine Copenheaver
*Assistant Examiner*—Cheryl Juska
*Attorney, Agent, or Firm*—Pauley Petersen Kinne & Fejer

[57] ABSTRACT

A unitary creped nonwoven web has a hydrophobic uncreped side and a creped side. The hydrophobic side includes looped regions. The creped side includes relatively narrow hydrophilic regions. The looped regions and creped regions act in conjunction with each other to form gradient capillaries, which urge the transfer of liquid toward the hydrophilic regions and away from the hydrophobic looped regions. The creped nonwoven web can be used as a top liner for an absorbent structure, such as a diaper, with the hydrophilic ends facing the absorbent core. When used in this fashion, the creped nonwoven web helps keep the wearer's skin dry.

49 Claims, 5 Drawing Sheets

CREPED NONWOVEN LINER WITH GRADIENT CAPILLARY STRUCTURE

This application is a continuation-in-part of U.S. patent application Ser. No. 08/962,992, filed on Oct. 31, 1997, the disclosure of which is incorporated by reference.

FIELD OF THE INVENTION

This invention relates to permanently creped nonwoven materials having low density, high permeability, improved loft and softness, looping, and out-of-plane fiber orientation and both hydrophobic and hydrophilic surfaces.

BACKGROUND OF THE INVENTION

Creped thermoplastic nonwoven materials are known from U.S. Pat. No. 4,810,556, issued to Kobayashi et al. In the disclosed process, a raw nonwoven fabric is coated with a lubricant and then pressed between a drive roll and a plate having a rough sandpaper-like surface. The plate is positioned near the drum and is substantially parallel or tangential to the outer surface of the drum. The raw nonwoven fabric is crinkled in a wavelike fashion in the direction of movement of the fabric by the frictional force caused by the pressing. The resulting creped fabric has wavelike crepes which contribute to softness. However, the creping accomplished by this process is not believed to be permanent. It is believed that the creping accomplished by this process can be removed or reduced significantly by subjecting the nonwoven web to mechanical stretching sufficient to flatten out the wavelike crepes. Also, the creping is naturally reduced over time during use of the fabric.

The creping of paper is also known in the art. However, paper has traditionally been creped using processes different from those used to crepe thermoplastic nonwoven webs. U.S. Pat. No. 3,879,257, issued to Gentile et al., discloses a process used for producing creped paper. A bonding material, preferably elastomeric, is applied to first and second surfaces of the paper so that it covers from about 15–60% of both paper surfaces and penetrates into about 10–40% of the paper thickness from both surfaces. Then, one side of the paper is adhered to a creping surface, such as a creping drum, using the bonding material to cause the adhesion. Then, the paper is creped from the creping surface using a doctor blade positioned at an angle to the surface. This creping method greatly disrupts the fibers in the unbonded regions of the paper increasing the overall softness, absorbency and bulk of the paper, and finely crepes the bonded areas of the paper to soften them.

There is a need or desire for a creped thermoplastic nonwoven web in which some or portions of the fibers are greatly disrupted to cause permanent creping. There is also a need or desire for a permanently creped nonwoven web containing individual filament loops, suitable for use as the female component in a hook-and-loop fastener. Furthermore, there is a need or desire for a permanently creped nonwoven web suitable for use as a liner, which has a hydrophobic side and a hydrophilic side.

SUMMARY OF THE INVENTION

The present invention is a permanently creped thermoplastic nonwoven web having interfilament bonded areas which are bent or oriented permanently out of plane, unbonded areas between the bonded areas, and substantial filament looping in the unbonded areas. The permanently creped web has low density, high permeability and excellent softness, and is useful as a loop material for a hook and loop fastener. The web also has a crinkled, puckered texture, and is useful for liners, transfer and surge layers, outercovers, wipes, and other fluid handling products. The web has a hydrophobic side and a hydrophilic side, thereby favoring the movement of liquid water and moisture away from the skin surface in end use applications.

The starting material used to make the invention includes an uncreped hydrophobic thermoplastic nonwoven web which can, for instance, be a hydrophobic thermoplastic spunbonded web or a hydrophobic thermoplastic meltblown web. The nonwoven web is at least partially coated on one side with a hydrophilic adhesive, so that about 5–100% (preferably 10–70%) of the total surface area on one side is coated, and about 0–95% (preferably 30–90%) of the area is uncoated. The adhesive renders one side of the web hydrophilic. The nonwoven web also possesses interfilament bonding, in the form of a pattern called the "nonwoven web bond pattern," which is imparted during manufacture of the nonwoven web. The adhesive penetrates the nonwoven web to some extent in the coated areas, causing increased interfilament bonding in those areas. The at least partially coated side of the thermoplastic nonwoven web is then placed against a creping surface, such as a creping drum, and is peelably bonded to the creping surface. The creping surface is preferably heated, and is moved (e.g. rotated) in a machine direction. As the creping surface moves, the leading edge of the nonwoven web bonded to the surface is creped off using a doctor blade.

The doctor blade penetrates the adhesive coating underneath the web and lifts the nonwoven web off the drum, resulting in permanent filament bending in the bonded areas corresponding to the nonwoven web bond pattern, and permanent looping of the filaments in the unbonded areas. Only one side of the web need be creped in this fashion to form a loop material suitable for use as the female component in a hook and loop fastener, and for forming a liner suitable for use in diapers and other surge applications.

The resulting creped sheet has a soft, contoured hydrophobic side with relatively large pores, that is intimately connected to a hydrophilic side having smaller pores. The size of the pores decreases from the hydrophobic side to the hydrophilic side of the creped nonwoven sheet. The structure provides low liner saturation, leading to low skin hydration. Because of the unique surface topography caused by the creped pattern, only the hydrophobic areas will be in contact with the wearer's skin, contributing to a dry feel.

With the foregoing in mind, it is a feature and advantage of the invention to provide a permanently creped nonwoven web having low density, high permeability and excellent softness and texture.

It is also a feature and advantage of the invention to provide a permanently creped nonwoven web having a looped structure suitable for use as the female component of a hook and loop fastener.

It is also a feature and advantage of the invention to provide a permanently creped nonwoven web having textured hydrophilic and hydrophobic surfaces suitable for use in liners, transfer and surge layers, outercovers, wipers, and other fluid handling materials.

The foregoing and other features and advantages of the invention will become further apparent from the following detailed description of the presently preferred embodiments, read in conjunction with the accompanying drawings. The detailed description and drawings are intended to be merely illustrative rather than limiting, the scope of the invention being defined by the appended claims and equivalents thereof.

DEFINITIONS

"Permanently creped" refers to a creped nonwoven web having bonded and unbonded areas, in which the bonded areas are permanently bent out-of-plane and the unbonded portions are permanently looped, such that the nonwoven web cannot be returned to its original uncreped state by applying a mechanical stress.

"Crepe level" is a measure of creping and is calculated according to the following equation:

$$\text{Crepe level } (\%) = \frac{\text{Speed of Creping Surface minus speed of winduup reel for the creped web}}{\text{Speed of Creping Surface}} \times 100$$

"Bent out-of-plane" refers to a bonding or orientation of portions of the nonwoven web in a direction away from the plane in which the nonwoven web substantially lies before being subjected to the creping process. As used herein, the phrase "bent out-of-plane" generally refers to nonwoven webs having creped portions bent at least about 15 degrees away from the plane of the uncreped nonwoven web, preferably at least about 30 degrees.

"Looped" refers to unbonded filaments or portions of filaments in a creped nonwoven web which define an arch, semi-circle or similar configuration extending above the plane of the uncreped nonwoven web, and terminating at both ends in the nonwoven web (e.g. in the bonded areas of the creped nonwoven web).

"Nonwoven web" means a web having a structure of individual fibers or threads which are interlaid, but not in an identifiable, repeating manner. Nonwoven webs have been, in the past, formed by a variety of processes such as, for example, melt-blowing processes, spunbonding processes and bonded carded web processes.

"Nonwoven web bond pattern" is a pattern of interfilament bonding in the nonwoven web which is imparted during manufacture of the nonwoven web.

"Meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, possibly to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, the disclosure of which is hereby incorporated by reference.

"Microfibers" means small diameter fibers having an average diameter not greater than about 100 microns, for example, having an average diameter of from about 0.5 microns to about 50 microns, or more particularly, an average diameter of from about 4 microns to about 40 microns.

"Spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbonded nonwoven webs is illustrated in patents such as, for example, in U.S. Pat. No. 3,802,817 to Matsuki et al. and U.S. Pat. No. 5,382,400 to Pike et al. The disclosures of these patents are hereby incorporated by reference.

"Polymer" generally includes, but is not limited to, homopolymers, copolymers, such as, for example, block, graft, random and alternating copolymers, terpolymers, etc. and blends and modifications thereof. Furthermore, the term "polymer" shall include all possible geometrical configurations of the material. These configurations include, but are not limited to, isotactic, syndiotactic and random symmetries.

"Bicomponent fibers" refers to fibers which have been formed from at least two polymers extruded from separate extruders but spun together to form one fiber. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or may be a side-by-side arrangement or an "islands-in-the-sea" arrangement. Bicomponent fibers are taught in U.S. Pat. No. 5,108,820 to Kaneko et al., U.S. Pat. No. 5,336,552 to Straek et al., and European Patent 0586924. For two component fibers, the polymers may be present in ratios of 75/25, 50/50, 25/75 or any other desired ratios.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

"Hydrophilic" refers to a surface or material that has an affinity for water, and is wettable by water. Some hydrophilic materials are capable of absorbing water, dissolving in water, and/or swelling.

"Hydrophobic" refers to a surface or material that is poorly wetted by water, has little or no affinity for water, and tends to repel water.

"Gradient capillary" refers to a unitary structure having a hydrophobic end and a hydrophilic end, with a transformation from hydrophobic to hydrophilic occurring between the two ends.

"Consisting essentially of" does not exclude the presence of additional materials which do not significantly affect the desired characteristics of a given composition or product. Examples of such materials include, without limitation, pigments, antioxidants, stabilizers, surfactants, waxes, flow promoters, particulates and materials added to enhance processability of the composition.

DETAILED DESCRIPTION OF THE PRESENTLY PREFERRED EMBODIMENTS

Figure 1:
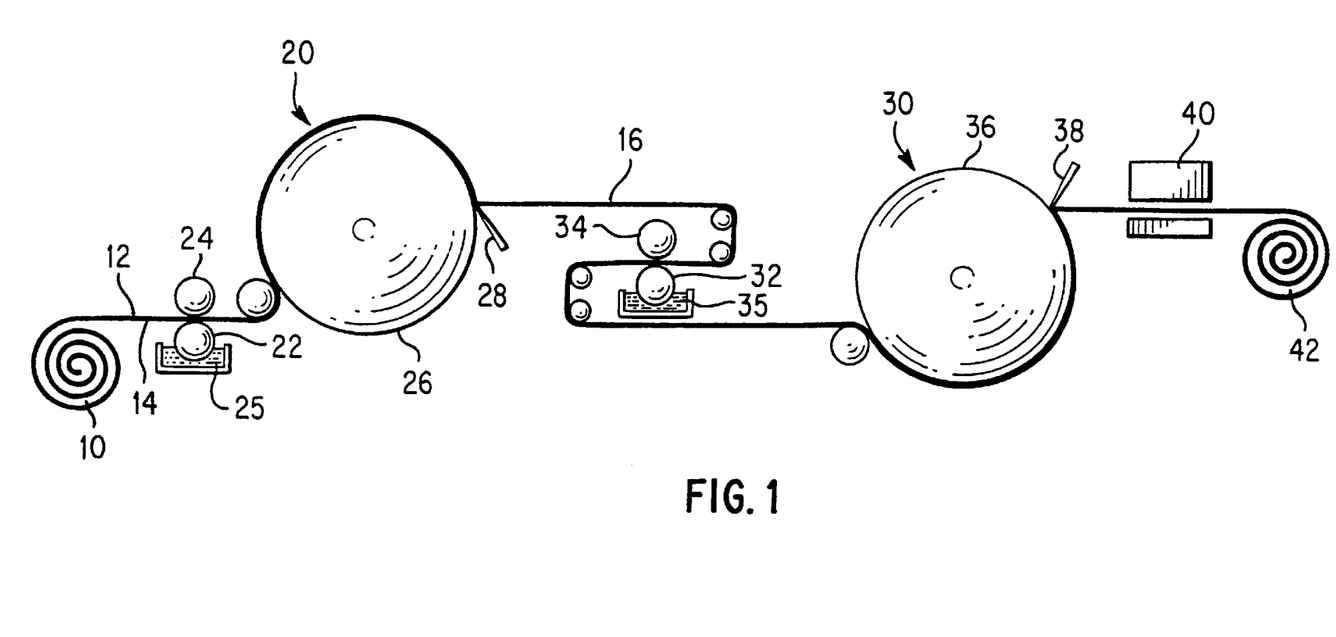
FIG. 1 is a schematic side view of one type of an apparatus for producing a permanently creped nonwoven web of the invention.

FIG. 1 illustrates a process for preparing a creped nonwoven web of the invention, which can be a creped spunbonded web. The nonwoven web is preferably creped on only one side, using a hydrophilic adhesive. The nonwoven web can be creped on its other side, using a hydrophobic adhesive. A nonwoven web 12, which can be a spunbonded web, is unwound from a supply roll 10. The nonwoven web 12 may be passed through a first creping station 20, a second creping station 30, or both. If it is desired to crepe the nonwoven web 12 on only one side, it may be passed through either the first creping station 20 or the second creping station 30, with one creping station or the other being bypassed. If it is desired to crepe the nonwoven web 12 on both sides, it may be passed through both creping stations.

A first side 14 of the web 12 may be creped using the first creping station 20. The creping station 20 includes first a printing station including a lower patterned or smooth printing roller 22, an upper smooth anvil roller 24, and a printing bath 25, and also includes a dryer roller 26 and associated creping blade 28.

The rollers 22 and 24 nip the web 12 and guide it forward. As the rollers 22 and 24 turn, the patterned or smooth printing roller 22 dips into bath 25 containing a hydrophilic adhesive material, and applies the adhesive material to the first side 14 of the web 12 in a partial coverage at a plurality of spaced apart locations, or in a total coverage. The hydrophilic adhesive-coated web 12 is then passed around drying drum 26 whereupon the adhesive-coated surface 14 becomes adhered to the roller 26. The first side 14 of the web 12 is then creped (i.e. lifted off the drum and bent) using doctor blade 28.

It is generally preferred that the nonwoven web 12 be creped on only one side. However, a second side 16 of the web 12 may be creped using the second creping station 30, with the aid of a hydrophobic adhesive. The second creping station 30 includes a second printing station including a lower patterned or smooth printing roller 32, an upper smooth anvil roller 34, and a printing bath 35, and also includes a dryer drum 36 and associated creping blade 38. The rollers 32 and 34 nip the web 12 and guide it forward. As the rollers 32 and 34 turn, the printing roller 32 dips into bath 35 containing a hydrophobic adhesive material, and applies the hydrophobic adhesive to the second side 16 of the web 12 in a partial or total coverage. The adhesive-coated web 12 is then passed around drying roller 36 whereupon the hydrophobic adhesive-coated surface 16 becomes adhered to the roller 36. The second side 16 of the web 12 is then creped (i.e. lifted off the drum surface and bent) using doctor blade 38.

After creping, the nonwoven web 12 may be passed through a chilling station 40 and wound onto a storage roll 42. The level of creping is affected by the surface speed of the windup roll 42 relative to the surface speed of the creping drum 36, according to the equation presented above. The surface speed of the windup roll 42 is slower than the surface speed of the creping drum 36, and the difference between the two speeds affects the level of creping. The level of creping should generally be about 5–75%, preferably about 15–60%, most preferably about 25–50%.

The nonwoven web 12 may be any type of thermoplastic nonwoven web. For instance, web 12 may be a spunbonded web, a meltblown web, a bonded carded web, or a combination including any of the following. Preferably, the web 12 is a spunbonded web. A wide variety of thermoplastic polymer materials can be used to make the nonwoven web 12. Exemplary polymer materials include without limitation, polypropylene, polyethylene (high and low density), ethylene copolymers with $C_3$–$C_{20}$ α-olefins, propylene copolymers with ethylene or $C_4$–$C_{20}$ α-olefins, butene copolymers with ethylene, propylene, or $C_5$–$C_{20}$ α-olefins, polyvinyl chloride, polyesters, polyamides, polyfluorocarbons, polyurethane, polystyrene, polyvinyl alcohol, caprolactams, and cellulosic and acrylic resins. Bicomponent and biconstituent thermoplastic webs may also be utilized, as well as webs containing blends of one or more of the above-listed thermoplastic polymers. The web 12 may have a basis weight of about 0.2–2.0 ounces per square yard (osy) before creping, desirably about 0.3–1.5 osy.

A wide variety of hydrophilic adhesive bonding materials may be applied to the first side 14 of the web 12 to reinforce the fibers of the web 12 at the locations of adhesive application, to render the first side 14 hydrophilic, and to temporarily adhere the first side 14 of the web 12 to the surface of the drum 26. Example of suitable hydrophilic adhesives includes without limitation a material sold under the trade name HYCAR® by the B.F. Goodrich Company. HYCAR® is an acrylic polymer emulsion containing a 20:1 weight ratio of a latex acrylic polymer and an additional surfactant. The additional surfactant is sold under the trade name AHCOVEL® by Imperial Chemical Industries, Ltd. and is composed of a 55:45 mixture of hydrogenated ethoxylated castor oil and sorbitan monooleate. The effective wetting agent is the castor oil derivative.

Other hydrophilic latex-based adhesives may also be used including, for example, other acrylic based latices. One such acrylic-based latex is sold by Air Products Co. under the trade name AIRFLEX® A-105. Hydrophilic styrene butadiene rubber-based adhesives may also be employed. Other surfactants may also be employed in combination with the adhesives, which surfactants are useful as wetting or rewetting agents. Another example of a suitable surfactant is TRITON® X-100, sold by the Union Carbide Corp.

The above-described adhesives can be described generally as latex-based adhesives which are rendered hydrophilic by the inclusion of hydrophilic surfactants. As an alternative to employing a surfactant, the adhesive itself may be composed of one or more hydrophilic polymer materials. An example of a hydrophilic polymer-based adhesive is AIR-VOL® 523, sold by Air Products Co. This adhesive is based on polyvinyl alcohol having a medium molecular weight and about 88% hydrolysis. In other embodiments of the adhesive, polyvinyl alcohol may be combined with sorbitol at weight ranges of about 70–100% polyvinyl alcohol and 0–30% sorbitol.

Other hydrophilic polymer-based adhesives include without limitation adhesives based on natural gums (e.g., guar gum and pectin), starch and starch derivatives, and cellulose derivatives (e.g., methylcellulose, carboxymethyl cellulose, and hydroxyalkyl celluloses), and combinations thereof. Hydrophilic adhesives may be applied using the printing technique described above or, alternatively, by melt blowing, melt spraying, dripping, splattering, or any technique capable of producing a partial or total adhesive coverage on the first side 14 of the web 12.

When the second side 16 of the web 12 is creped a wide variety of hydrophobic adhesive bonding materials may be utilized to reinforce the fibers of the web 12 at the locations of adhesive application, and to temporarily adhere the web 12 to the surface of the second creping drum 36. Elastomeric adhesives (i.e. materials capable of at least 75% elongation without rupture) are especially suitable. Suitable materials include without limitation aqueous-based styrene butadiene adhesives (not treated with hydrophilic surfactants), neoprene, polyvinyl chloride, vinyl copolymers, polyamides, and ethylene vinyl terpolymers. A suitable hydrophobic adhesive material is an acrylic polymer emulsion (not treated with hydrophilic surfactants) sold by the B.F. Goodrich Company under the trade name HYCAR®. The hydrophobic adhesive may be applied using the printing technique described above or may, alternatively, be applied by meltblowing, melt spraying, dripping, splattering, or any technique capable of forming a partial or total adhesive coverage on the second side 16 of the web 12.

The percent adhesive coverage of the web 12 generally affects the level of creping obtained. Generally the adhesive should cover about 5–100% of the web surface, preferably about 10–70% of the web surface, more preferably about 25–50% of the web surface. In the presently preferred embodiment, the web 12 is coated with hydrophilic adhesive and creped on only one side. The web 12 may be coated with hydrophobic adhesive and creped on the other side, however. The adhesive should also penetrate the nonwoven web 12 in the locations where the adhesive is applied. Generally, the adhesive should penetrate through about 10–50% of the nonwoven web thickness, although there may be greater or less adhesive penetration at some locations.

Figure 5:
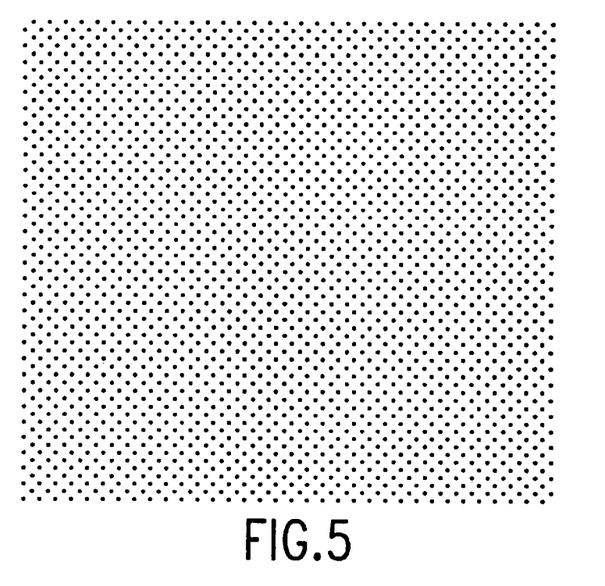
FIGS. 5–7 illustrate three nonwoven web bonding patterns used during preparation of the creped nonwoven web of the invention.

The resulting creped nonwoven web product has a controlled pattern creping which corresponds generally to the nonwoven web interfilament bond pattern and, to a lesser degree, the applied adhesive material. A presently preferred nonwoven web bonding pattern is a regular point bond pattern referred to as the "HP" pattern, shown in FIG. 5. The HP pattern has a bond area of 19–32%, a bond density of 204 points/in$^2$, and a point height or depth of 0.030 in. This bond pattern results in the formation of regular fiber loops and excellent bulk.

Figure 6:
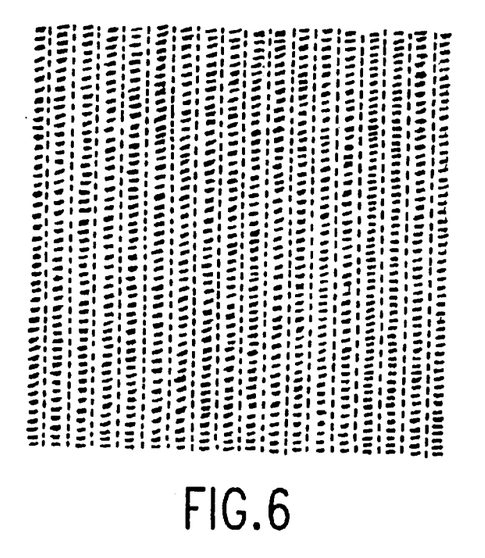

Another suitable nonwoven web bond pattern is the "rib knit" pattern shown in FIG. 6. The rib knit pattern is designed for a knitted fabric appearance. The pattern has a bond area of 10–20%, a bond density of 212 bond points/in$^2$, and a bond point height or depth of 0.044 in. This pattern provides creped nonwoven fabrics with excellent softness.

Figure 7:
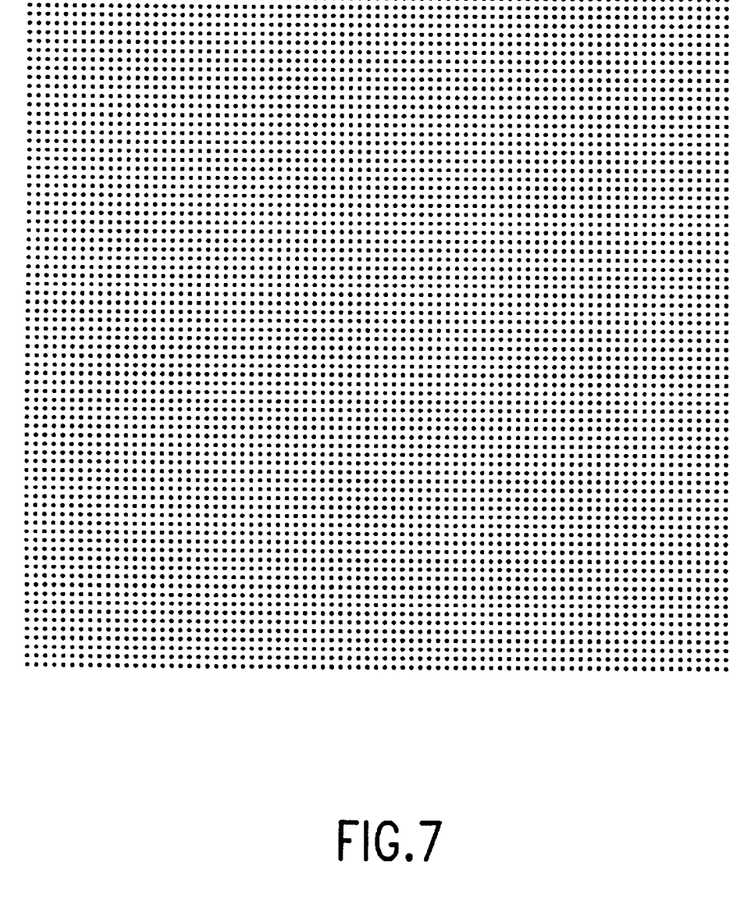

Another suitable nonwoven web bond pattern, characterized by elliptical-shaped point bonds, is the "wire weave" pattern shown in FIG. 7. The wire weave pattern has a bond area of 15–21%, a bond density of 302 point/in$^2$, and a bond point height or depth of 0.038 in. This pattern is designed to provide a nonwoven fabric with a woven look, and results in creped nonwoven fabrics having good softness, bulk, and fiber looping.

The creping of the nonwoven web is primarily manifested in the bonded areas of the base ("raw") nonwoven web, corresponding to the nonwoven web bond pattern. As a result of the creping, the bonded regions are bent out of plane so as to cause permanent creping of the web, and the formation of filament looped regions in the unbonded regions alternating with (in between) the creped bonded regions.

Figure 2:
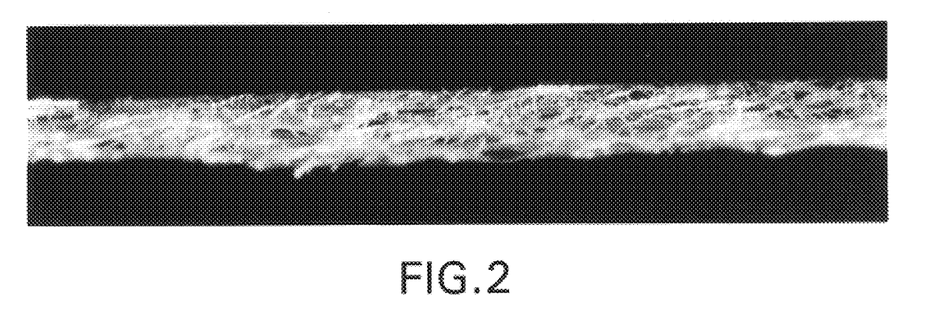
FIG. 2 is a greatly enlarged sectional view photograph of an uncreped nonwoven web.
Figure 3:
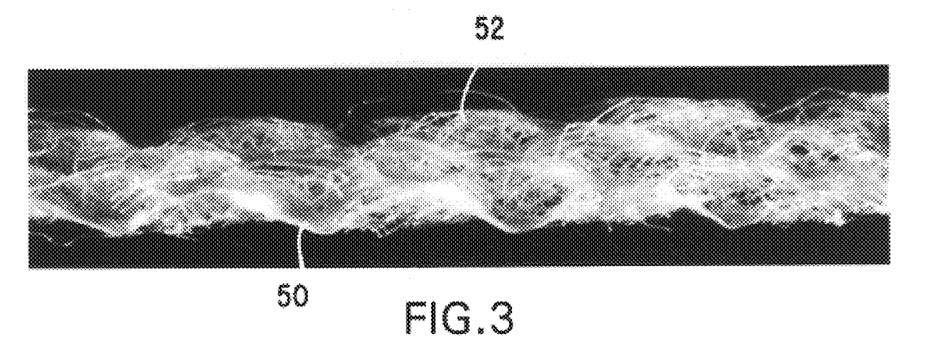
FIG. 3 is a greatly enlarged sectional view photograph of a permanently creped nonwoven web of the invention, creped on one side to a 25% crepe level.
Figure 4:
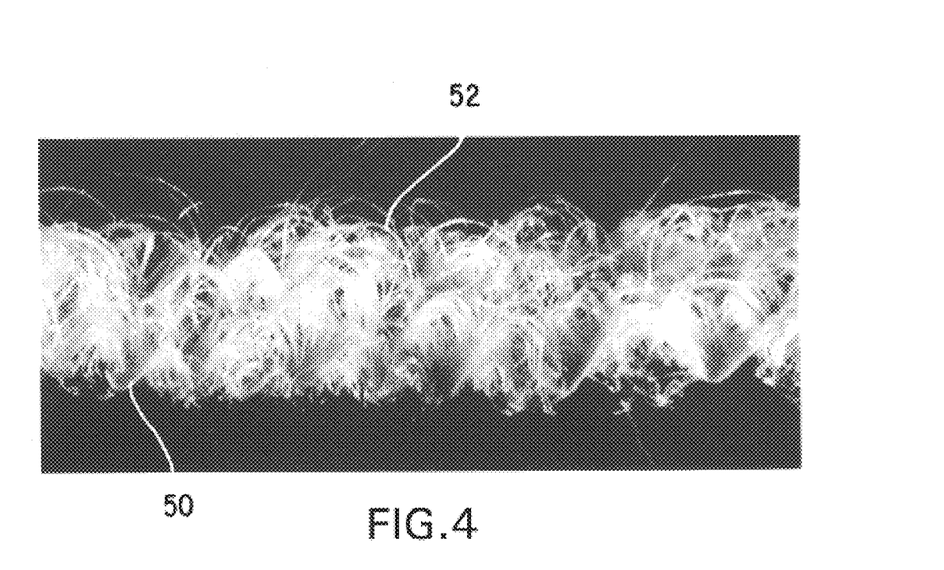
FIG. 4 is a greatly enlarged sectional view photograph of a permanently creped nonwoven web of the invention, creped on one side to a 50% crepe level.

FIG. 2 illustrates an uncreped nonwoven web, which is a spunbonded web. FIGS. 3 and 4 illustrate the same spunbonded web creped according to the invention at creping percentages of 25% and 50%, respectively. As shown in FIGS. 3 and 4, each of the creped webs has creped nonwoven web bond regions 50 which are bent permanently out of plane due to the creping. Looped regions 52 corresponding to the unbonded, non-creped regions exist between the creped regions. The creped regions 50 include tightly bonded filament regions, while the looped regions 52 include loose filament regions. The individual filament loops terminate at both ends in the adhesive-reinforced regions, and are anchored in the adhesive-reinforced regions. As seen in FIGS. 3 and 4, the degree of looping increases substantially when the level of creping is increased from 25% to 50%. The completeness of the loops suggest that there is very little fiber breakage.

As is further apparent from FIGS. 3 and 4, the creping provides an effective gradient pore or capillary structure whose contour corresponds to the contour of creped regions 50 and looped regions 52, and whose individual capillaries are in the form of cup-shaped protuberances. Each capillary is narrower at an end corresponding to a creped region 50, and is wider at an end defined by surrounding looped regions 52. The narrower ends defined by creped regions 50, which have been covered with hydrophilic adhesive resulting in the creping, provide the hydrophilic mechanism away from the wearer's skin that helps remove water and keep it away from the skin. The wider ends defined by looped regions 52, which have not been covered with adhesive and are not bent out of plane, help propel the water away from the skin toward the hydrophilic tops of looped regions 52. The hydrophilic creped regions 50 of the nonwoven web are positioned away from the wearer's skin, and the hydrophobic looped regions 52 are against the wearer's skin.

Put another way, the creped nonwoven web structure includes a large pore, generally hydrophobic top side and a smaller pore, more hydrophilic bottom side. This creates a capillarity gradient, with more capillarity at the bottom compared to the top. In use, the liquid is drawn away from the top and is prevented from coming back to rewet the skin, hence insuring a much drier top surface and correspondingly drier skin.

The resulting unitary creped nonwoven web has low density, high permeability, excellent surface and bulk softness, excellent fluid transfer properties, recoverable stretch properties, surface topology, and permanent out-of-plane fiber orientation. The creped nonwoven web can be used in a variety of end products including inkers, transfer and surge layers, outercovers, wipers, and other fluid handling materials. One excellent use of the creped nonwoven web is as a top cover component for a diaper. The creped nonwoven web is positioned on the top side of a diaper with the hydrophilic creped protuberances facing the absorbent core of the diaper, and with the uncreped hydrophobic looped side facing away from the absorbent core and adapted to contact the wearer's skin. The creped nonwoven web is also useful as a top cover for other personal care absorbent products including training pants, incontinence garments, and tampons. In each case, the creped nonwoven web is positioned so that liquid migrates away from the wearer's skin and toward the hydrophilic creped regions 50 of the nonwoven web.

Figure 8:
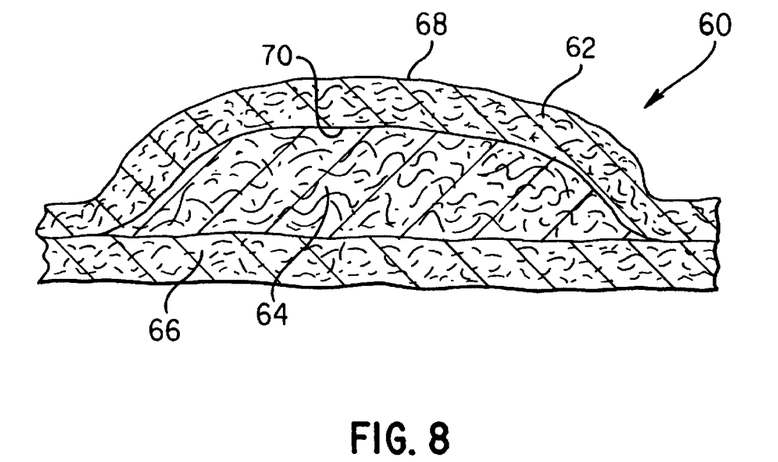
FIG. 8 is a sectional view of an absorbent article which utilizes the creped nonwoven web of the invention as a top layer.

FIG. 8 illustrates an absorbent article 60, which can be a diaper. The article 60 includes a top liner 62, an absorbent core 64, and a back sheet 66. The liner 62 includes the nonwoven web of the invention having the hydrophilic creped protuberances facing the absorbent core 64. The outer surface 68 of the liner 62 is hydrophobic and looped, and touches the wearer's skin. The inner creped surface 70, having the hydrophilic regions, faces the absorbent core. The gradient effect of the liner 62, which progresses from hydrophobic to hydrophilic, urges any liquid matter away from the wearer's skin and toward the absorbent core 64.

Because of the looping caused in the uncreped, unbonded regions, the creped nonwoven web 12 is also highly suitable for use as the female ("loop") component in a hook-and-loop type fastener. The loops in the web 12 engage the male fastener components in a peelable fashion, such that the hook and loop fastener can be opened and closed a number of times.

In another embodiment, the nonwoven web can be mechanically stretched in the machine direction (causing the web to contract or neck in the cross direction) before applying the adhesive and creping the web. The resulting necked web product is stretchable in the cross direction. Mechanical stretching of the web is accomplished using processes well known in the art. For instance, the web may be pre-stretched by about 0–100% of its initial length in the machine direction to obtain a necked web that can be stretched (e.g. by about 0–100%) in the cross direction. Preferably, the web is stretched by about 10–100% of its initial length, more commonly by about 25–75% of its initial length. The stretched web is then dimensionally stabilized to some extent, first by the adhesive which is applied to the web, and second by the heat which is imparted from the creping drum. This stabilization sets the cross-directional stretch properties of the web. The machine direction stretch is further stabilized by the out-of-plane deformation of the nonwoven web bonded areas that occurs during creping.

The pre-stretching of the web can be used to optimize and enhance physical properties in the creped nonwoven product including softness, bulk, stretchability and recovery, permeability, basis weight, density, and liquid holding capacity. The elastic behavior of the creped nonwoven web can be further enhanced by laminating it to a layer of elastic material, for example, an isotropic elastic web or a layer of elastic strands.

EXAMPLES

The following measurement procedures were used to test the fabrics of the Examples. The basis weight is determined by measuring the mass of a creped nonwoven web sample and dividing it by the area covered by the nonwoven web sample. Generally, the basis weight increases at higher levels of creping due to crinkling and bulking of the web.

Figure 9:
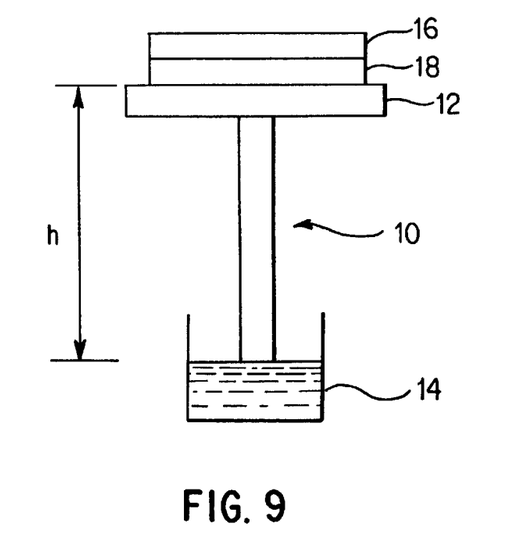
FIG. 9 is a schematic illustration of a test apparatus used to measure liner saturation.

The liner saturation test measures the level of saturation in the liner after it has been saturated and allowed to desorb. Low liner saturation is important in reducing skin hydration. The test apparatus is illustrated in FIG. 9. The apparatus 10 includes a porous plate 12 charged with a 0.9% saline solution. The porous plate 12 is raised to a height h of 10 cm above a fluid reservoir 14, hence providing 10 cm capillary suction, simulating an absorbent system. The liner 16 to be tested is weighed and placed on top of a surge material 18, and both webs are placed on the porous plate. Both liner and surge material are 3 inches in diameter. 50 ml of saline is then poured over the liner and surge and allowed to saturate both webs. The porous plate then drains excess liquid and any liquid that can be removed from both surge and liner due to the capillary suction of the porous plate. A 0.3 psi load is placed over the webs for 5 minutes to allow equilibrium to occur. At the end of the 5 minute period, the liner is carefully removed and immediately weighed. The percentage gain in the weight of the liner is reported as percentage liner saturation.

The surge material used was a 2.5 osy bonded carded web composed of 60% by weight 3 denier bicomponent polyethylene/polypropylene fibers from Chisso Corporation, and a 40% by weight 6 denier polyethylene terephthalate fibers. The web density was 0.034 grams/cc.

The skin dryness test is described as follows:

Method: Armband Trans Epidermal Water Loss (TEWL) Protocol;

Reference: F. J. Akin, J. T. Lemmen, D. L. Bozarth, M. J. Garofalo, G. L. Grove: A refined method to evaluate diapers for effectiveness in reducing skin hydration using the adult forearm, *Skin Research and Technology* 1997; 3: 173–176, Denmark.

This method is a full product test and actually measures the level of hydration on human skin after a prescribed method of loading the diaper. The product is worn (on the forearm) for one hour after which the level of hydration on the skin is measured by an evaporimeter. The measurement unit is $g/m^2$ hour. Lower numbers indicate lower skin hydration. The following results are from full product test wherein only the liner was changed.

Example 1

Control

For use as a control, a polypropylene spunbond web having a basis weight of 0.5 ounces per square yard (osy) and 2.2 denier fibers was topically treated with 0.3% by weight Ahcovel Base N-62, available from Hodgson Chemical Co. Ahcovel Base N-62 is a surfactant used to promote topical wettability, and is a blend of ethoxylated hydrogenated castor oil and sorbitan monooleate. The spunbond web was not creped. The resulting liner was tested for liner saturation and skin dryness.

Example 2

A polypropylene spunbond web having a basis weight of 0.4 osy and 3.5 denier fibers was printed on one side with a fluid containing 35% by weight HYCAR® 26684 latex adhesive solids sold by B.F. Goodrich Co. and 65% by weight water. The print pattern uses a 60×90 diamond pattern. The wet pickup was 1% by weight of the web. The web was creped on the coated side to a 25% crepe level. The resulting liner was tested for liner saturation and skin dryness.

Example 3

A polypropylene spunbond web having a basis weight of 0.3 osy and 2.2 denier fibers was printed on one side with a fluid containing 35% by weight HYCAR® 26884 latex adhesive solids, 1% by weight Ahcovel Base N-62, and 64% by weight water. The print pattern was an overall dot pattern. The wet pickup was 3% by weight of the web. The web was creped on the coated side to a 25% crepe level. The resulting liner was tested for skin dryness.

Example 4

A polypropylene spunbond web having a basis weight of 0.3 osy and 2.2 denier fibers was printed on one side with a fluid containing 35% by weight HYCAR® 26884 latex adhesive solids and 65% by weight water. The print pattern was an overall dot pattern. The wet pickup was 3% by weight of the web. The web was creped to a 25% level. The resulting liner was tested for skin dryness.

Example 5

A polypropylene spunbond web having a basis weight of 0.4 osy and 3.2 denier fibers was topically treated with 0.37% by weight of a surfactant containing 0.28 parts by weight Ahcovel Base N-62 and 0.09 parts by weight Masil SF-19 (an ethoxylated trisiloxane available from PPG). The web was then printed on one side with a fluid containing 35% by weight HYCAR® 26884 latex adhesive solids and 65% by weight water. The print pattern was an overall dot pattern. The wet pickup was 3% by weight of the web. The web was creped to a 25% level. The resulting liner was tested for skin dryness.

The test results are reported below.

|  | Liner Saturation, percent | Skin Dryness, TEWL change from control, grams/$m^2$-hour |
| --- | --- | --- |
| Example 1 | 120 | 0 |
| Example 2 | 83 | −2.4 |
| Example 3 | Not measured | −5.5 |
| Example 4 | Not measured | −6.3 |
| Example 5 | Not measured | −7.1 |

The foregoing examples reflect a significant decrease in liner saturation, and improvement in skin dryness, when the creped nonwoven material of the invention is used as the liner.

While the embodiments of the invention disclosed herein are presently considered preferred, various improvements and modifications can be made without departing from the spirit and scope of the invention. The scope of the invention is indicated in the appended claims, and all changes that fall within the meaning and range of equivalents are intended to be embraced therein.

I claim:

1. A permanently creped thermoplastic nonwoven web comprising:
   a hydrophobic nonwoven fibrous web at least partially covered on one side with a hydrophilic creping adhesive, the nonwoven fibrous web having permanently creped interfilament-bonded regions alternating with non-creped regions of no interfilament bonding;
   the nonwoven web having a nonwoven web bond pattern which effects the interfilament-bonded regions;
   the interfilament-bonded regions being creped so as to exhibit permanent out-of-plane bending;
   the regions of no interfilament bonding including a multiplicity of filament loops terminating in the interfilament-bonded regions.

2. The permanently creped thermoplastic nonwoven web of claim 1, having a level of creping of about 5–75%.

3. The permanently creped thermoplastic nonwoven web of claim 1, having a level of creping of about 15–60%.

4. The permanently creped thermoplastic nonwoven web of claim 1, having a level of creping of about 25–50%.

5. The permanently creped thermoplastic nonwoven web of claim 1, comprising a nonwoven web selected from the group consisting of a spunbonded web, a meltblown web, a carded web, and combinations thereof.

6. The permanently creped thermoplastic nonwoven web of claim 1, comprising a nonwoven spunbonded web.

7. The permanently creped thermoplastic nonwoven web of claim 1, wherein the web comprises a polymer selected from the group consisting of propylene polymers and copolymers.

8. The permanently creped thermoplastic nonwoven web of claim 1, wherein the web comprises a polymer selected from the group consisting of ethylene polymers and copolymers.

9. The permanently creped thermoplastic nonwoven web of claim 1, wherein the web comprises a polymer selected from the group consisting of butene polymers and copolymers.

10. The permanently creped thermoplastic nonwoven web of claim 1, wherein the adhesive comprises a latex and a hydrophilic surfactant.

11. The permanently creped thermoplastic nonwoven web of claim 10, wherein the latex comprises an acrylic polymer.

12. The permanently creped thermoplastic nonwoven web of claim 10, wherein the latex comprises a styrene-butadiene polymer.

13. The permanently creped thermoplastic nonwoven web of claim 10, wherein the surfactant comprises a mixture of hydrogenated ethoxylated castor oil and sorbitan monooleate.

14. The permanently creped thermoplastic nonwoven web of claim 1, wherein the creping adhesive comprises a hydrophilic polymer.

15. The permanently creped thermoplastic nonwoven web of claim 14, wherein the hydrophilic polymer comprises polyvinyl alcohol.

16. The permanently creped thermoplastic nonwoven web of claim 15, wherein the hydrophilic polymer further comprises sorbitol.

17. The permanently creped thermoplastic nonwoven web of claim 14, wherein the hydrophilic polymer comprises a material selected from the group consisting of natural gums, starches, starch derivatives, cellulose derivatives, and combinations thereof.

18. The permanently creped thermoplastic nonwoven web of claim 1, wherein the nonwoven fibrous web is mechanically stretched before the nonwoven fibrous web is at least partially covered with the adhesive.

19. The permanently creped thermoplastic nonwoven web of claim 18, wherein the nonwoven fibrous web is stretched in the machine direction before the nonwoven web is at least partially covered with the adhesive.

20. The permanently creped thermoplastic nonwoven web of claim 18, wherein the nonwoven fibrous web is mechanically stretched by about 10–100% of an initial length of the nonwoven fibrous web before the nonwoven fibrous web is at least partially covered with the adhesive.

21. The permanently creped thermoplastic nonwoven web of claim 18, wherein the nonwoven fibrous web is mechanically stretched by about 25–75% of an initial length of the nonwoven fibrous web before the nonwoven fibrous web is at least partially covered with the adhesive.

22. A permanently creped thermoplastic nonwoven web having a creped side and an uncreped side;
the thermoplastic nonwoven web comprising a hydrophobic thermoplastic material;
the creped side comprising a plurality of creped interfilament-bonded regions alternating with non-creped regions of no interfilament bonding;
the uncreped side comprising a plurality of looped regions;
the creped regions further comprising a hydrophilic creping adhesive and having hydrophilic properties;
the looped regions having hydrophobic properties.

23. A permanently creped thermoplastic nonwoven web having a first creped side and an opposing creped side;
the nonwoven web comprising a hydrophobic thermoplastic material;
the first creped side comprising a plurality of creped regions;
the creped regions further comprising a hydrophilic creping adhesive and having hydrophilic properties;
the opposing creped side comprising a hydrophobic creping adhesive and having hydrophobic properties.

24. The creped thermoplastic nonwoven web of claim 23, wherein the hydrophobic adhesive comprises a material selected from the group consisting of styrene butadiene adhesives, neoprene, polyvinyl chloride, vinyl copolymers, polyamides, ethylene vinyl terpolymers, and combinations thereof.

25. The creped thermoplastic nonwoven web of claim 23, comprising a nonwoven web selected from the group consisting of a spunbonded web, a meltblown web, a carded web, and combinations thereof.

26. The creped thermoplastic nonwoven web of claim 23, comprising a nonwoven spunbonded web.

27. The creped thermoplastic nonwoven web of claim 23, wherein the web comprises a polymer selected from the group consisting of propylene polymers and copolymers.

28. The creped thermoplastic nonwoven web of claim 23, wherein the web comprises a polymer selected from the group consisting of ethylene polymers and copolymers.

29. The creped thermoplastic nonwoven web of claim 23, wherein the web comprises a polymer selected from the group consisting of butene polymers and copolymers.

30. The creped thermoplastic nonwoven web of claim 23, wherein the hydrophilic adhesive comprises a latex and a hydrophilic surfactant.

31. The creped thermoplastic nonwoven web of claim 30, wherein the latex comprises an acrylic polymer.

32. The creped thermoplastic nonwoven web of claim 30, wherein the latex comprises a styrene-butadiene polymer.

33. The creped thermoplastic nonwoven web of claim 30, wherein the surfactant comprises a mixture of hydrogenated ethoxylated castor oil and sorbitan monooleate.

34. The creped thermoplastic nonwoven web of claim 23, wherein the hydrophilic adhesive comprises a hydrophilic polymer.

35. The creped thermoplastic nonwoven web of claim 34, wherein the hydrophilic polymer comprises polyvinyl alcohol.

36. The creped thermoplastic nonwoven web of claim 35, wherein the hydrophilic polymer further comprises sorbitol.

37. The creped thermoplastic nonwoven web of claim 34, wherein the hydrophilic polymer comprises a material selected from the group consisting of natural gums, starches, starch derivatives, cellulose derivatives, and combinations thereof.

38. The creped thermoplastic nonwoven web of claim 23, wherein the nonwoven fibrous web is mechanically pre-stretched.

39. A permanently creped thermoplastic nonwoven web having an effective gradient capillary structure;
the thermoplastic nonwoven web comprising a thermoplastic material and having a creped side and an uncreped side;
the creped side comprising a plurality of creped interfilament-bonded regions alternating with non-creped regions of no interfilament bonding;
the web further comprising a plurality of gradient capillaries, each having a relatively hydrophobic end and a relatively hydrophilic end;
the gradient capillaries operating to urge liquid transfer toward the hydrophilic ends and away from the hydrophobic ends.

40. The permanently creped thermoplastic nonwoven web of claim 39, wherein the gradient capillaries comprise cup-shaped forms, such that the relatively hydrophobic end is wider than the relatively hydrophilic end of each capillary.

41. The permanently creped thermoplastic nonwoven web of claim 39, wherein the thermoplastic nonwoven web comprises a hydrophobic thermoplastic material.

42. The permanently creped thermoplastic nonwoven web of claim 39, wherein the hydrophilic ends of the capillaries are covered with a hydrophilic creping adhesive.

43. The permanently creped thermoplastic nonwoven web of claim 41, wherein the hydrophilic ends of the capillaries are covered with a hydrophilic creping adhesive.

44. An absorbent article comprising a top liner, an absorbent core and a back sheet;
the top liner including a hydrophobic outer surface and an inner surface facing the absorbent core;
the outer surface including a plurality of looped regions;
the inner surface including a plurality of creped interfilament-bonded regions alternating with non-creped regions of no interfilament bonding;
the looped regions and the creped regions defining capillaries therebetween;
each capillary having a relatively narrow end and a relatively wider end;
the relatively narrow ends having hydrophilic properties;
the relatively wider ends having hydrophobic properties.

45. The absorbent article of claim 44, wherein the capillaries comprise gradient capillaries operating to urge liquid transfer toward the absorbent core.

46. The absorbent article of claim 44, wherein the top liner comprises a thermoplastic hydrophobic nonwoven material.

47. The absorbent article of claim 44, wherein the relatively narrow ends further comprise a hydrophilic adhesive material.

48. The absorbent article of claim 46, wherein the relatively narrow ends further comprise a hydrophilic adhesive material.

49. The absorbent article of claim 44, wherein the top liner comprises a thermoplastic nonwoven web creped on one side.

* * * * *